United States Patent [19]

Ogawa et al.

[11] Patent Number: 4,737,259

[45] Date of Patent: Apr. 12, 1988

[54] ELEMENT FOR ELECTROPHORESIS

[75] Inventors: Masashi Ogawa, Asaka; Masakazu Hashiue; Yuzo Mizobuchi, both of Kaisei, all of Japan

[73] Assignee: Fuji Photo Film Co., Ltd., Kanagawa, Japan

[21] Appl. No.: 948,401

[22] Filed: Dec. 29, 1986

Related U.S. Application Data

[63] Continuation of Ser. No. 711,613, Mar. 14, 1985, abandoned.

[30] Foreign Application Priority Data

Mar. 15, 1984 [JP] Japan .................................. 59-50293
Mar. 15, 1984 [JP] Japan .................................. 59-50294

[51] Int. Cl.$^4$ ............................................... C07K 3/14
[52] U.S. Cl. ................................ 204/299 R; 428/448; 428/477.7
[58] Field of Search ..................... 204/299 R, 182.8; 428/477.7, 448

[56] References Cited

U.S. PATENT DOCUMENTS

| | | | |
|---|---|---|---|
| 3,875,044 | 4/1975 | Renn et al. | 204/299 R |
| 3,922,432 | 11/1975 | Renn | 428/327 |
| 3,960,499 | 6/1976 | White | 422/55 |
| 4,415,428 | 11/1983 | Nochumson et al. | 204/299 R |
| 4,548,869 | 10/1985 | Ogawa et al. | 428/474.7 |
| 4,548,870 | 10/1985 | Ogawa et al. | 428/474.7 |
| 4,579,783 | 4/1986 | Ogawa et al. | 428/475.2 |
| 4,600,641 | 7/1986 | Ogawa et al. | 428/355 |
| 4,657,656 | 4/1987 | Ogawa | 204/299 R |

*Primary Examiner*—G. L. Kaplan
*Attorney, Agent, or Firm*—Jules E. Goldberg

[57] ABSTRACT

An element for electrophoresis suitably employable for electrophoresis of biopolymers such as proteins, as well as for the determination of the base sequence of DNA, RNA, their fragments, and their derivatives, which comprises a plastic support, a nonconductive metal oxide layer, and an electrophoresis medium layer comprising an aqueous polyacrylamide gel formed by crosslinking polymerization of an acrylamide compound and a crosslinking agent in the presence of water, which are superposed in this order. The electrophoresis medium layer may contain a water-soluble polymer and agarose. The medium layer may contain a modifier such as an anionic surfactant, formamide or urea.

11 Claims, No Drawings

ELEMENT FOR ELECTROPHORESIS

This is a continuation of application Ser. No. 711,613 filed Mar. 14, 1985 and now abandoned.

BACKGROUND OF OF THE INVENTION

1. Field of the Invention

This invention relates to an element for electrophoresis, and more particularly relates to an element for electrophoresis suitably employable for electrophoresis of biopolymers, such as, proteins, as well as for determination of the base sequence of DNA, RNA, their fragments, and their derivatives.

2. Description of Prior Arts

For the analysis of biopolymers, such as, proteins, the electrophoresis can be carried out in the following manner.

A membrane medium for electrophoresis prepared by coating or casting a membrane-forming material, such as, agar, cellulose, cellulose acetate, starch, silica gel or polyacrylamide gel over a support, such as, a glass plate or a transparent plastic sheet (or film) and the membrane are impregnated with a buffer solution; on the medium is applied a substance to be analyzed (sample); the applied sample is developed (or resolved) on or in the medium by applying a voltage between both ends of the support. A dye is applied thereto and then the optical density of the dyed sample is measured to quantitatively determine the developed components of the sample.

Details of the electrophoresis and medium therefor are given in "Experimental Text for Electrophoresis (5th revision) edited by Electrophoresis Society of Japan (Bunkodo, 1975), "*Modern Electrophoresis*" edited by *Aoki & Nagai (Hirokawa Shoten,* 1973), etc.

Recently, electrophoresis has been employed to analyze substances originating from a living body; for instance, the analyses of proteins originating from a living body are generally performed in the course of biochemical analysis for diagnosis purposes.

As the membrane or sheet for electrophoresis, a filter paper was previously employed, but recently an agarose membrane or a polyacrylamide gel membrane (or medium) have been employed because of their advantageous properties. Particularly, polyacrylamide gel membranes exhibiting a molecular sieve function have been widely employed recently. The polyacrylamide gel membrane can be prepared by crosslinking polymerization of a monomer, such as, acrylamide and a two-functional crosslinking agent, such as, N,N'-methylenebisacrylamide under oxygen-free conditions in the presence of water and a polymerization catalyst.

In the course of the preparation of the polyacrylamide gel membrane, a modifier, such as, an anionic surfactant is incorporated into the membrane in certain cases. Since only a small amount of the modifier is required for the preparation of the gel membrane for protein analysis, the modifier can be incorporated into the membrane by applying an aqueous modifier solution onto the wet gel membrane or immersing the gel membrane in an aqueous modifier solution.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3–1 mm); sealing the gel-forming solution from oxygen; and causing the crosslinking polymerization to prepare the desired gel membrane. This procedure employing glass plates is disadvantageous because the glass plate is easily breakable and rather heavy, so that careful handling is required. Thus, the procedure employing glass plates presents difficulties when used to prepare the polyacrylamide gel membrane on a mass scale.

For the reason described above, it is desired to replace the glass plates as the polyacrylamide gel membrane supports with a light-weight plastic material. However, acceptable plastic material support such as, a polyethylene terephthalate (PET) sheet, exhibits poor adhesion between the gel membrane and the plastic material support which needs to be improved for the following reasons.

The prepared polyacrylamide gel is horizontally or vertically placed for performing slab electrophoresis. The electrophoresis is performed for a certain period of time under predetermined conditions, and the desired analysis of the components originating from the living body is done after dyeing the electrophoresed gel membrane with, for instance, Ponceau 3R (Ciba-Geigy), Coomassie Brilliant Blue G-250 (ICI), or silver. The gel membrane is apt to separate from the support in the dyeing procedure even when employing the glass plate support. Therefore, the dyeing procedure requires highly skilled operation to prevent the separation of the gel membrane from the support. The poor affinity of the plastic material support for the polyacrylamide gel membrane makes it more difficult to handle the element for electrophoresis without separation of the support from the gel membrane.

In the method for determination of base sequence of DNA, RNA, their fragments, and their derivatives according to the post-label method, the procedure of slab electrophoresis using a polyacrylamide gel membrane has become essential. Since the study in the genetic engineering technology has advanced recently, quick determination of the base sequence of DNA, etc., is highly desired.

The polyacrylamide gel membrane employable for the above purpose also can be prepared by crosslinking polymerization of a monomer, such as, acrylamide and a two-functional crosslinking agent, such as, N,N'-methylenebisacrylamide under an oxygen-free condition in the presence of water and a polymerization catalyst. In the course of the preparation of the polyacrylamide gel membrane, a modifier, such as, urea or formamide is generally incorporated into the membrane.

The polyacrylamide gel membrane prepared as above is employed for electrophoresis in the manner, such as, described below.

The polyacrylamide gel membrane is vertically placed in the form of being sandwiched between the glass plates, and firstly, a pre-electrophoresis procedure is carried out. Then, a certain amount of a sample ($^{32}$P-labeled DNA cleaved by the Maxam-Gilbert method) is introduced into sample slots provided on the membrane, and the electrophoresis is carried out. After the electrophoresis is carried out for a certain period of time (e.g., approx. 6–12 hours), one glass plate is removed carefully. Then, the exposed gel membrane is covered with a polymer film, such as, a poly(vinylidene chloride) film and subjected to the autoradiographic process. The autoradiographic process is carried out by the following procedures: A radiographic film and an intensifying screen are superposed successively on the film covering the gel membrane, thereby exposing the radiographic film to the gel membrane at a low temperature (e.g., $-80°$ C.) for a certain period of time (e.g., approx. 10-20 hours). After the exposing procedure, the radiographic film is developed, and the resolved pattern reproduced on the film is studied for determination of the base sequence of DNA, etc.

Since the autoradiographic process requires a long period as described above, it has been desired that the operational period is shortened. Moreover, enhancement of resolution accuracy in the detection of the resolved pattern is desired.

It is known that the resolution accuracy can be enhanced by applying the autoradiographic process to the gel membrane in the dry state. The procedure for drying the gel membrane can be carried out as follows. The gel membrane having been subjected to electrophoresis is immersed in a 10% aqueous acetic acid solution so as to fix the resolved DNA cleavage products as well as to remove the modifier, such as, urea from the membrane. Since the adhesion between the glass plate and the gel membrane is weak or negligible, the gel membrane easily separates from the glass plate and floats in the solution. The separated gel membrane is carefully taken out, placed on a filter paper, and dried under reduced pressure. The membrane is thus dried and fixed onto the filter paper. The autoradiographic process applied to the dry membrane shows a highly enhanced resolution. However, the drying process has drawbacks, that the separation and drying stages require highly trained skill and careful handling, and even then, the membrane is sometimes broken in these stages.

SUMMARY OF THE INVENTION

An object of the present invention is to provide an element for electrophoresis having improved adhesion between the support and the aqueous gel medium, such as, in the form of a membrane under wet conditions.

Another object of the present invention is to provide an element for electrophoresis which is substantially free from separation of the aqueous gel medium layer from the support in stages, such as, a posttreatment stage in an aqueous solution and a subsequent drying stage.

The present invention provides an element for electrophoresis comprising:
 (I) a plastic material support;
 (II) a nonconductive metal oxide layer; and
 (III) a medium layer for electrophoresis comprising an aqueous polyacrylamide gel formed by crosslinking polymerization of an acrylamide compound and a crosslinking agent in the presence of water,
which are superposed in this order.

The element for electrophoresis of the invention comprises the three-layers structure of a support layer, a nonconductive metal oxide layer (which serves as an adhesive layer) and an electrophoresis medium layer. Such three-layers structure is highly resistant to separation between the support layer and the electrophoresis medium layer in a variety of stages. Accordingly, the medium layer is resistant to breaking during the analytical procedure, and the element is much easier to handle. Moreover, the electrophoresis element of the present invention can be prepared by forming the electrophoresis layer on a horizontally arranged metal oxide-plated support. Therefore, the element for electrophoresis of the invention can be advantageously prepared on a mass scale.

DETAILED DESCRIPTION OF THE INVENTION

Examples of the support employable for the preparation of the element for electrophoresis of the present invention include a variety of polymer materials in the form of a sheet (the term "sheet" includes a film and a plate). Examples of the polymer materials include polyethylene terephthalate, polycarbonate of Bisphenol A, polyvinyl chloride, vinylidene chloride—vinyl chloride copolymer, polymethyl methacrylate, polyethylene, polypropylene, cellulose acetates, and cellulose acetate propionate. Preferred is a polyethylene terephthalate sheet.

The support employed in the invention can be subjected to glow discharge treatment prior to the provision of the nonconductive metal oxide layer thereon.

The glow discharge treatment can be applied onto the support under such conditions that the surface of the support can be made hydrophilic. Glow discharge treatments for making a surface of a polymer material hydrophilic are known and can be used for the glow discharge treatment of the support.

The glow discharge treatment can be applied to another surface of the support. Thus, if the glow discharge treatment is applied to the reverse side surface, said surface can be advantageously combined with a glass plate without an adhesive when the element for electrophoresis of the invention is to be tentatively arranged on a glass plate.

The support generally has a thickness in the range of approx. 50 to 500 $\mu$m, and preferably approx. 70 to 300 $\mu$m.

On the support, a nonconductive metal oxide layer serving as an adhesive layer is provided. The metal oxide layer can be provided on a surface of the support through vapor deposition.

There is no specific limitation on the metal oxide employable in the invention, so long as it is substantially nonconductive. Examples of nonconductive metal oxides include $SiO_2$, $TiO_2$, $MgO$, $Al_2O_3$, $BeO$, $ZrO_2$, $WO_2$, and $Ta_2O_3$. $SiO_2$ and $TiO_2$ are most preferred.

The vapor deposition of metal oxide can be performed by known methods, such as, the electron beam method or a sputtering process. Since the vapor deposition technology for depositing a metal or metal oxide on a solid article is conventional, further description is not given.

The metal oxide layer generally has a thickness in the range of approx. 0.05 to 3 $\mu$m, and preferably approx. 0.1 to 2 $\mu$m.

The nonconductive metal oxide layer can be treated with a silane-type coupling agent, such as, vinyl silane in advance of the subsequent deposition of the electrophoresis medium layer. The silane-type coupling agent can be coated over the surface of the metal oxide layer.

The aqueous gel medium layer is now described in more detail.

The aqueous gel medium (may be referred to herein as "gel membrane") employed in the invention is a medium layer consisting essentially of an aqueous polyacrylamide gel formed by crosslinking polymerization of an acrylamide compound and a crosslinking agent in the presence of water.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" includes both an "aqueous solution" and an "aqueous dispersion", unless otherwise indicated. The term "aqueous medium" includes both water as well as an aqueous mixture of water and an organic solvent, the organic solvent being optionally added.

Examples of the acrylamide compound employable in the present invention include acrylamide and its homologues, such as, N-methylacrylamide, N,N-dimethylacrylamide, N-(hydroxymethyl)acrylamide and diacetonacrylamide, as well as methacrylamide and its homologues. These compounds can be employed independently or in combination. Acrylamide is most preferred among these acrylamide compounds, and said acrylamide can be also preferably employed in combination with one or more other acrylamide compounds.

As the crosslinking agent used to obtain the polyacrylamide gel membrane, known crosslinking agents described, for instance, in "Electrophoresis" 1981, 2, 213–228 can be employed singly or in combination. Examples of the crosslinking agent include bifunctional compounds, such as, N,N'-methylenebisacrylamide (BIS), N,N'-propylenebisacrylamide (PBA), di(acrylamide dimethyl)ether (i.e., N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamide (BAC). The crosslinking agent can be employed in an amount of approx. 2 to 30 wt.%, preferably approx. 3 to 10 wt.%, based on the total weight of the monomer (i.e., acrylamide compound) and the crosslinking agent. The gel concentration preferably is in the range of approx. 2 to 30 wt/v % (total weight of monomer and crosslinking agent per total volume of gel membrane comprising monomer, crosslinking agent and aqueous medium), the concentration being expressed in accordance with the definition indicated by S. Hjerten in "Arch. Biochem. Biophys." 1 (Suppl.), 147 (1962).

The element for electrophoresis of the present invention can be employed for analysis of proteins and conjugated proteins (e.g., lipoproteins, glycoproteins, etc.) and the medium (gel membrane) of the element may comprise an anionic surfactant as a modifier. The use of the anionic surfactant is generally essential or preferable for the electrophoretic analyses of proteins or conjugated proteins, because it contributes to the separation of the protein and conjugated protein and determination of the molecular weight of these proteins. However, the medium of the element for electrophoresis may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion, such as, sodium ion, potassium ion, or lithium ion. Sodium ion is preferred from an economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for the determination of the molecular weight thereof. The anionic surfactant (modifier) can be contained in the gel-forming solution in an amount of approx. 0.05 to 2.0 wt/v % (weight per volume of the gel-forming solution), and preferably approx. 0.1 to 1.5 wt/v %.

The element for electrophoresis of the invention also can be employed for the determination of base sequence of DNA, RNA, their fragments, and their derivatives. For this purpose, a compound containing at least one carbamoyl group is generally incorporated into the electrophoresis medium as a modifier. Examples of the modifier include urea and formamide. Urea is most preferred. The modifier can be used in an amount of approx. 40 to 60 wt.% based on the volume of the aqueous gel containing the monomer and crosslinking agent. When urea is used as the modifier, the amount generally ranges from approx. 6 moles (approx. 360 g.) per one liter of the aqueous gel containing the monomer and crosslinking agent to the saturation amount, and preferably from approx. 7 moles (approx. 420 g.) to the saturation amount.

The gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithicthreitol and 2-mercaptoethanol.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols, such as, polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in the range of approx. 2 to 100 wt.%, preferably, approx. 5 to 50 wt.%, based on the total weight of the monomer and crosslinking agent.

The addition of a water-soluble polymer serves to impart elasticity to the gel membrane, and the thus modified gel membrane is still elastic even if it is dried. Thus, the gel membrane is so improved as to be free from brittleness, whereby the gel membrane becomes hardly resistant to breaking. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose, such as, low-electroendosmosis agarose, medium-electroendosmosis agarose, or high-electroendosmosis agarose can be used. Examples of agarose employable in the invention include the agaroses disclosed in Japanese Patent Provisional Publication Nos. 55(1980)-5730, 55(1980)-110946 (corresponding to U.S. Pat. No. 4,290,911 and GB Pat. No. 2 042 571A), 57(1982)-502098 (WO 82/02599, U.S. Pat. No. 4,319,976), etc. The amount of agarose to be added ranges from approx. 0.2 to 2 wt/v %, preferably from approx. 0.3 to 1.2 wt/v % based, on the volume of the aqueous gel containing the monomer and crosslinking agent. It becomes possible by the addition of agarose to control the viscosity of the gel-forming solution through changing the temperature of the solution, thus suppressing the flowability of the solution as well as facilitating the formation of the gel membrane.

A pH buffer agent can be contained in the gel membrane of the invention.

In the gel membrane of the element for electrophoresis of protein and protein derivatives, a buffer agents which is able to buffer a solution to a range of pH 2.5 to 10.0 can be incorporated. Such buffer agents are described in publications such as "Chemistry Handbook, Fundamental Edition" compiled by The Chemical Society of Japan (Maruzen Ltd., Tokyo, 1966) pages 1312–1320; "Modern Electrophoresis" edited by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroxymethyl)methyl]-3-aminopropanesulfonic acid (TAPS) or its salt. Preferable examples of the buffer agent include potassium dihydrogenphosphate-disodium hydrogenphosphate, Tris-sodium borate, Tris-sodium borate-EDTA.2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, sodium salt of TAPS, etc.

In the gel membrane of the element of electrophoresis of DNA and the like, a buffer agent which is able to buffer a solution to a range of pH 8.0 to 9.0, preferably pH 8.2 to 8.3 can be incorporated. Such buffer agents are described in the aforementioned publications.

Examples of the buffer agent include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl methyl]-3-aminopropanesulfonic acid (TAPS) or its NA or K salt; as well as an acid, an alkali, and a salt employable in combination with the compounds. Preferable examples of the buffer agent include Tris, boric acid-EDTA.2Na (pH 8.3).

The gel membrane of the element of the invention is formed by radical crosslinking polymerization between the monomer, such as, acrylamide with the bifunctional compound (crosslinking agent) in an aqueous medium in which the water-soluble polymer and agarose preferably are dissolved almost homogeneously. The thus obtained gel is assumed to have a structure in which the water-soluble polymer and agarose are dispersed in the three dimensional crosslinked polymer formed by the reaction of the monomer and cross-linking agent, and the dispersed water-soluble polymer and agarose entangle with the three dimensionally crosslinked polymer structure.

The crosslinking polymerization can be initiated by a known method, for instance, in the presence of a peroxide and/or under irradiation of ultra-violet rays. The reaction can be further accelerated by heat and irradiation with ultra-violet rays.

As the polymerization catalyst, known low temperature-polymerization initiators such as those described in "Electrophoresis" 1981, 2, 213–219, ibid. 1981, 2, 220–228; and "Modern Electrophoresis" edited by Aoki & Nagai (Hirokawa Shoten, 1973) can be used. Examples of the initiator include a mixture of $\beta$-dimethylaminopropionitrile (DMAP) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultra-violet rays. The radical reaction initiator can be employed in the amount of approx. 0.3 to 5 wt. %, preferably approx. 0.5 to 2 wt. %, based on the total amount of the monomer and crosslinking agent.

A polyol compound, such as, glycerol or ethylene glycol can be contained in the aqueous gel membrane of the element of the invention as a wetting agent. The polyol compound can be introduced in an amount of approx. 5 to 40 wt.% based on the volume of the aqueous gel membrane. Glycerol is particularly preferable among the polyol compounds. The addition of the wetting agent serves to keep the gel membrane from excessive dryness possibly caused by evaporation of water during storage of the medium, thus preventing the medium from turning brittle or cracking due to the excessive dryness. This proves the physical properties of the gel membrane.

The gel membrane of the element of the invention can be prepared by a process in which a gel forming solution is coated by a known method on an electric insulation support having a nonconductive metal oxide layer thereon. The gel forming solution is then crosslinked and polymerized on the surface of the support.

When the gel forming solution is crosslinked on the surface of the support, the surface of the gel forming solution layer can be covered with a covering material, such as, a film, sheet, or plate. The same material used for the support can be employed as the covering material. The covering materials may be previously treated by glow discharge treatment to have a hydrophilic surface. The covering material has a thickness of not more than 300 $\mu$m, and preferably, has approx. 4 to 200 $\mu$m, from the practical viewpoint.

If the covering material is thick (e.g., approx. 70 to 300 $\mu$m), the element of the present invention can be prepared by the following steps: the gel forming solution is first coated on the covering material and crosslinked thereon to form the desired gel medium layer, and then a support having the metal oxide layer thereon is provided on the gel medium layer.

The gel membrane of the invention can be employed for horizontal or vertical electrophoresis, disc electrophoresis, etc. by known methods including those described above.

The medium for electrophoresis provided in the element of the present invention is strongly bound to the support through the use of the specific adhesive layer. Accordingly, the element for electrophoresis of the present invention is always kept in the form of an integrated unit in the course of normal practice. For this reason, the complicated procedures conventionally required in the electrophoresis of proteins, conjugated proteins, DNA, DNA cleavage products, etc. can be simplified by the use of the element for electrophoresis according to the present invention.

The present invention will be more clearly understood with reference to the following examples.

EXAMPLE 1

A surface of a colorless transparent polyethylene terephthalate sheet (thickness 180 μm) was made hydrophilic by irradiation of ultraviolet rays. On the surface of the sheet (support) was deposited $SiO_2$ to have a thickness of approx. 0.5 μm by means of an electron beam depositing apparatus. The thickness of the deposited layer was measured by means of a quartz oscillation type film thickness head monitor.

On the $SiO_2$ deposited surface of the support was formed a polyacrylamide gel membrane of 0.5 mm thickness by coating an aqueous solution containing 9.5 g. of acrylamide, 0.5 g. of BIS, 3.58 g. of disodium hydrogenphosphate 12 hydrates, 0.33 g. of sodium dihydrogenphosphate 2 hydrates, and 0.10 g. of sodium dodecylsulfate (SDS) in 100 ml. volume after addition of 1.3 ml of ammonium peroxodisulfate (5 weight %) and 33 μl. of TEMED, both being the polymerization initiator. Thus, an element for electrophoresis was obtained.

A control protein was electrophoresed on the polyacrylamide gel membrane. The element was then immersed in an aqueous Coomasie Blue R-250 (Colour Index Constitution Number 42660) solution (0.1%) for dyeing. In the dyeing process, the adhesiveness between the support and the polyacrylamide gel membrane was observed.

The gel membrane was completely bound to the support during the dyeing process. No unsatisfactory results were observed in the electrophoresis in the use of said element.

Moreover, the gel membrane of the element could be easily cut with a blade without detrimental effect to the shape of the membrane. Also, separation did not occur between the support and the gel membrane due to the cutting procedure.

EXAMPLE 2

The procedure of Example 1 was repeated except that the thickness of the $SiO_2$ layer was changed to approx. 1.0 μm.

The obtained element was subjected to electrophoresis and subsequently to the following dyeing steps as stated in Example 1.

The gel membrane was completely bound to the support during the dyeing process. No unsatisfactory results were observed in the electrophoresis using this element.

Moreover, the gel membrane of the element could be easily cut with a blade without detrimental effect to the shape of the membrane. Also, separation did not occur between the support and the gel membrane due to the cutting procedure.

COMPARISON EXAMPLE 1

The procedure of Example 1 was repeated except that $SiO_2$ layer was not provided on the support.

The element obtained was subjected to electrophoresis and subsequently to the dyeing steps as stated in Example 1.

A part of the gel membrane was separated from the support immediately after the element was immersed in the dyeing solution.

Moreover, the gel membrane of the element could be easily cut with a blade without detrimental effect to the shape of the membrane. Partial separation occurred between the support and the gel membrane due to the cutting procedure.

EXAMPLE 3

A surface of a colorless transparent polyethylene terephthalate sheet (thickness 180 μm) was made hydrophilic by irradiation with ultraviolet rays. $SiO_2$ was deposited on the surface of the sheet (support) to have a thickness of approx. 0.5 μm by means of an electron beam depositing apparatus. The thickness of the deposited layer was measured by means of a quartz oscillation type film thickness head monitor.

A polyacrylamide gel membrane having a thickness of 0.5 mm was formed on the surface of the $SiO_2$ by coating an aqueous solution containing 11.87 g. of acrylamide, 630 mg. of BIS, 42 g. of urea, 1.08 g. of tris(hydroxymethyl)aminomethane [CAS Registry No. 77-86-1], 0.55 g. of boric acid, and 93 mg of EDTA.Na salt in 100 ml. volume after the addition of 1.3 ml of ammonium peroxodisulfate (5 weight %) and 33 μl. of TEMED, both being the polymerization initiator to produce an element for electrophoresis.

A sample ($^{32}$P-DNA cleaved by the Maxam-Gilbert method) was electrophoresed on the polyacrylamide gel membrane for sequencing the DNA. After the electrophoresis was complete, the element was processed at −80° C. according to the conventional autoradiographic process.

The polyacrylamide gel membrane could be easily handled and presented no problems when subjected to the autoradiographic process.

The autoradiographic image obtained was as satisfactory as an autoradiographic image successfully obtained by the use of a gel membrane on the conventional glass plate.

Moreover, the gel membrane of the element could be easily cut with a blade without detrimental effect to the shape of the membrane. Also, separation did not occur between the support and the gel membrane due to the cutting procedure.

EXAMPLE 4

The procedure of Example 3 was repeated except that the thickness of $SiO_2$ layer was changed to approx. 1.0 μm.

The obtained element was subjected to electrophoresis and subsequently to the autoradiographic process as stated in Example 3.

The polyacrylamide gel membrane could be easily handled and presented no problems when subjected to the autoradiographic process.

The autoradiographic image obtained was as satisfactory as an autoradiographic image successfully obtained by the use of a gel membrane on the conventional glass plate.

Moreover, the gel membrane of the element could be easily cut with a blade without detrimental effect to the shape of the membrane. Also, separation did not occur between the support and the gel membrane due to the cutting procedure.

We claim:

1. An element for electrophoresis comprising in the following order:
   (I) a plastic material support layer;
   (II) a nonconductive oxide layer; and
   (III) a gel membrane for electrophoresis comprising an aqueous polyacrylamide gel formed by crosslinking polymerization of an acrylamide compound and a crosslinking agent in the presence of water.

2. The element for electrophoresis as claimed in claim 1, in which said nonconductive oxide layer is selected from the group consisting of $SiO_2$, $TiO_2$, MgO, $Al_2O_3$, BeO, $ZrO_2$, $WO_2$, and $Ta_2O_3$.

3. The element for electrophoresis as claimed in claim 2, in which said nonconductive oxide is selected from the group consisting of $SiO_2$ and $TiO_2$.

4. The element for electrophoresis as claimed in claim 1, in which said nonconductive oxide layer is treated with a vinyl silane on its surface.

5. The element for electrophoresis as claimed in any one of claims 1 to 4, in which the plastic material support layer is a polyethylene terephthalate sheet.

6. The element for electrophoresis as claimed in any one of claims 1 to 4, in which said gel membrane contains a water-soluble polymer and agarose.

7. The element for electrophoresis as claimed in any one of claims 1 to 4, in which said gel membrane contains an anionic surfactant.

8. The element for electrophoresis as claimed in claim 7, in which said anionic surfactant is an alkylsulfate.

9. The element for electrophoresis as claimed in claim 8, in which said alkylsulfate is sodium dodecylsulfate.

10. The element for electrophoresis as claimed in any one of claims 1 to 4, in which said gel membrane contains a compound having at least one carbamoyl group.

11. The element for electrophoresis as claimed in claim 10, in which said compound having at least one carbamoyl group is urea or formamide.

* * * * *